United States Patent [19]

Keller et al.

[11] Patent Number: 5,707,377
[45] Date of Patent: Jan. 13, 1998

[54] LIGATION CLIP REMOVER

[75] Inventors: John W. Keller, Huntington, Conn.; Daniel Helme, Warren, N.J.

[73] Assignee: American Cyanamid Company, Wayne, N.J.

[21] Appl. No.: 348,840

[22] Filed: Nov. 29, 1994

[51] Int. Cl.$^6$ ............................................. A61B 17/00
[52] U.S. Cl. .................. 606/138; 606/207; 132/330; 254/28
[58] Field of Search ............................. 606/138, 139, 606/142, 143, 151, 205–208; 254/28; 132/330

[56] References Cited

U.S. PATENT DOCUMENTS

| | | | |
|---|---|---|---|
| 3,344,649 | 10/1967 | Wood | 606/138 |
| 4,602,631 | 7/1986 | Kunatsu | 606/142 |
| 4,706,668 | 11/1987 | Backer | 606/142 |
| 5,403,327 | 4/1995 | Thornton et al. | 606/143 |
| 5,441,509 | 8/1995 | Vidal et al. | 606/151 |

*Primary Examiner*—Jeffrey A. Schmidt
*Attorney, Agent, or Firm*—Fitzpatrick, Cella, Harper & Scinto

[57] ABSTRACT

A ligation clip remover removes closed ligation clips from a ligated vessel. The remover includes a handle assembly having a squeezable trigger and a slender barrel assembly connected to the handle assembly. A clip separating mechanism is connected to a distal end of the barrel assembly, and a shaft is slidably disposed in the barrel assembly for operating the clip separating mechanism when the trigger is squeezed.

30 Claims, 7 Drawing Sheets

5,707,377

LIGATION CLIP REMOVER

BACKGROUND OF THE INVENTION

1. Field of the Invention

The subject invention relates generally to a medical instrument for use with ligation clips. More particularly, the invention is directed to a laparoscopic ligation clip remover for removing closed ligation clips from an occluded vessel.

2. Description of the Prior Art

Ligation clips have been used for many years to ligate, or occlude, vessels (e.g., a vein, an artery, a cystic duct, and the like) in a patient's body. During a surgical procedure, for example, a ligation clip is placed around the vessel and then closed to compress the vessel and stop the flow of fluid therethrough. In one application, a ligation clip can be used to clamp a severed blood vessel to stop the flow of blood.

Once a ligation clip is closed to ligate a vessel, it should, if designed and applied properly, remain closed around the vessel until either it is physically removed by one or more surgical instruments or it dissolves in the body as synthetic bioabsorbable polymer ligation clips are capable of doing. However, conventional surgical instruments used to remove known ligation clips are limited in their use, and generally are not designed for removing unique two-piece ligation clips of the type discussed below.

In providing an improved device for removing a closed ligation clip, the subject invention offers a simple, easy to use laparoscopic instrument for separating the closed ligation clip and enabling it to be easily removed from the vessel. The subject invention can conceivably be used to remove many types of known ligation clips because of its basic ability to separate two compressed parts, or arms. However, the subject invention is particularly useful for removing two-piece ligation clips of the type disclosed in U.S. patent application Ser. No. 07/908,938, which is assigned to the assignee of the subject invention.

The two-piece ligation clip disclosed in Ser. No. 07/906,938 is shown generally in FIGS. 9 and 10 to comprise a Y-shaped clamp 11 and a U-shaped clip body 13. As shown in FIG. 9, the open clamp is positioned around a vessel 15 to be occluded, and the clip body is engaged to either side of a lug, or trunnion, 17 on the clamp. The clip body 13 is urged forward relative to the clamp 11 to squeeze the clamp around the vessel as shown in FIG. 10. In the closed position, two arms 19 and 21 of the clamp 11 are closed together and secured by the clip body to the vessel. The design of the ligation clip assures that the clamp will not slide relative to the clip body once it is closed.

SUMMARY OF THE INVENTION

Accordingly, it is a general object of the present invention to provide a medical instrument that will provide an advancement in laparoscopic surgical procedures.

It is another object of the invention to provide a ligation clip remover that proficiently separates a closed ligation clip from a ligated vessel.

It is still a further object of the invention to provide a ligation clip remover designed for use with two-piece ligation clips.

In accordance with one aspect of the invention, a ligation clip remover comprises a handle assembly with a squeezable trigger, a barrel assembly rotatably connected to the handle assembly, and a shaft slidably housed in the barrel assembly and slidable by actuation of the trigger. A clip separator is engaged to a distal end of the barrel assembly and is closed by the sliding shaft.

In one preferred embodiment, the barrel assembly features a bayonet-type slot arrangement for rotatably securing itself to the handle assembly. In this manner, the barrel assembly can rotate freely about its longitudinal axis with respect to the handle assembly.

The clip separator is connected to a distal end of the barrel assembly and includes a spreader for spreading, or separating, the closed arms of the ligation clip. The spreader is pivotally mounted in the barrel assembly and, when at rest, is biased in an open position by a biasing spring. The shaft, in turn, is preferably spring loaded and slides forward by squeezing the trigger.

The spreader is formed of a lever having a proximal cam surface engaged by the sliding shaft and a hooked nose at its distal end. The hooked nose terminates in a pointed end for separating the first and second arms of the closed ligation clip.

In accordance with another aspect of the invention, a ligation clip remover comprises a handle having an actuator, extended barrel means connected to the handle, and clip separating means, secured in a distal end of the barrel means, for separating a closed ligation clip. In addition, actuating means, slidably housed in the barrel means, is operable by the actuator to actuate the clip separator.

In accordance with still another aspect of the invention, a ligation clip remover comprises a handle assembly having a squeezable trigger, a barrel assembly rotatably connected at its proximal end to the handle assembly, and clip separating means, secured in a distal end of the barrel, for separating a closed ligation clip. In addition, actuating means, slidably disposed within the barrel assembly, actuates the clip separating means when the trigger is squeezed.

These and other objects, aspects, features and advantages of the present invention will become apparent from the following detailed description of the preferred embodiment taken in conjunction with the accompanying drawings.

DESCRIPTION OF THE PREFERRED EMBODIMENTS

For ease of reference, as used herein the term "distal" will refer to that part of the ligation clip remover which is farthest from the surgeon-user, and the term "proximal" refers to that part of the remover which is closest to the surgeon-user.

Figure 1:
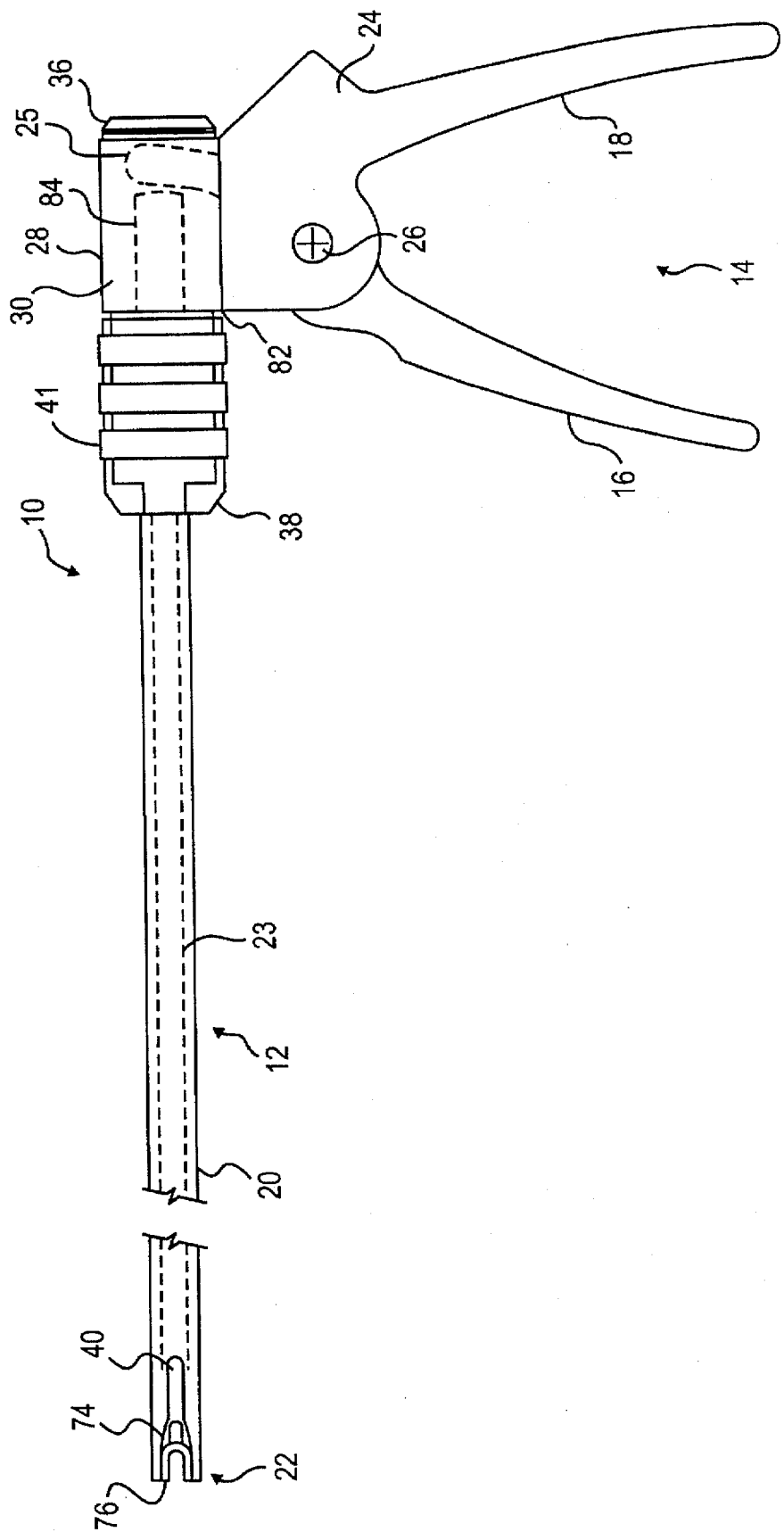
FIG. 1 is a side elevational view of a ligation clip remover in accordance with the present invention, showing a rotatable barrel assembly connected to a handle assembly.

The laparoscopic ligation clip remover 10 of the present invention is shown generally in FIG. 1 to comprise a barrel assembly 12 connected at its proximal end to a handle assembly 14, and a ligation clip separating mechanism 22 secured in a distal end of the barrel assembly. The handle assembly includes a pivotally mounted trigger 16 and a handle portion 18. As discussed in detail below, the barrel assembly is connected to the handle assembly in a manner that enables it to rotate freely about its longitudinal axis. The clip separating mechanism 22 is used for spreading, or separating, a closed ligation clip. A slidable shaft 23, shown in phantom lines in FIG. 1, slides back and forth within the barrel assembly to actuate the clip separating mechanism.

The barrel assembly 12 includes an elongated barrel 20 preferably of a diameter that allows it to be used in minimally-invasive surgery techniques. For example, the barrel could have a diameter of 8 mm so it can fit through a 10 mm cannula communicating from the exterior to the interior of the patient's body. The ligation clip remover is preferably made of surgical grade stainless steel.

In general terms, in one preferred use of the laparoscopic ligation clip remover, the barrel 20 is inserted into the patient's body through a cannula, and the clip separating mechanism is positioned relative to a closed ligation clip. The handle assembly is actuated by squeezing the trigger 16 to slide the shaft 23 forward and close the clip separating mechanism 22, thus separating the closed ligation clip and allowing it to be removed from the vessel.

Figure 3:
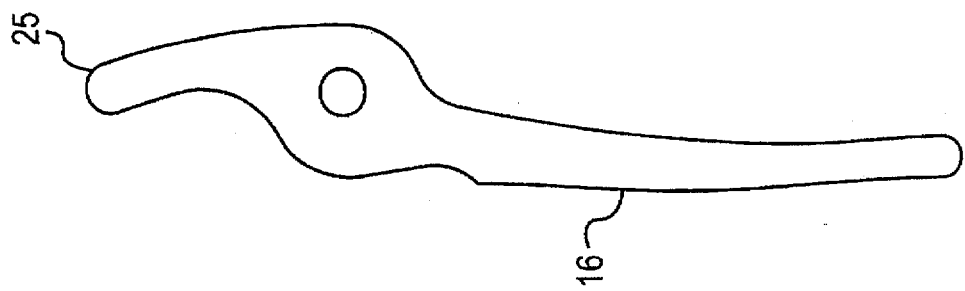
FIG. 3 is a side elevational view of part of the handle assembly in accordance with the present invention.
Figure 4:
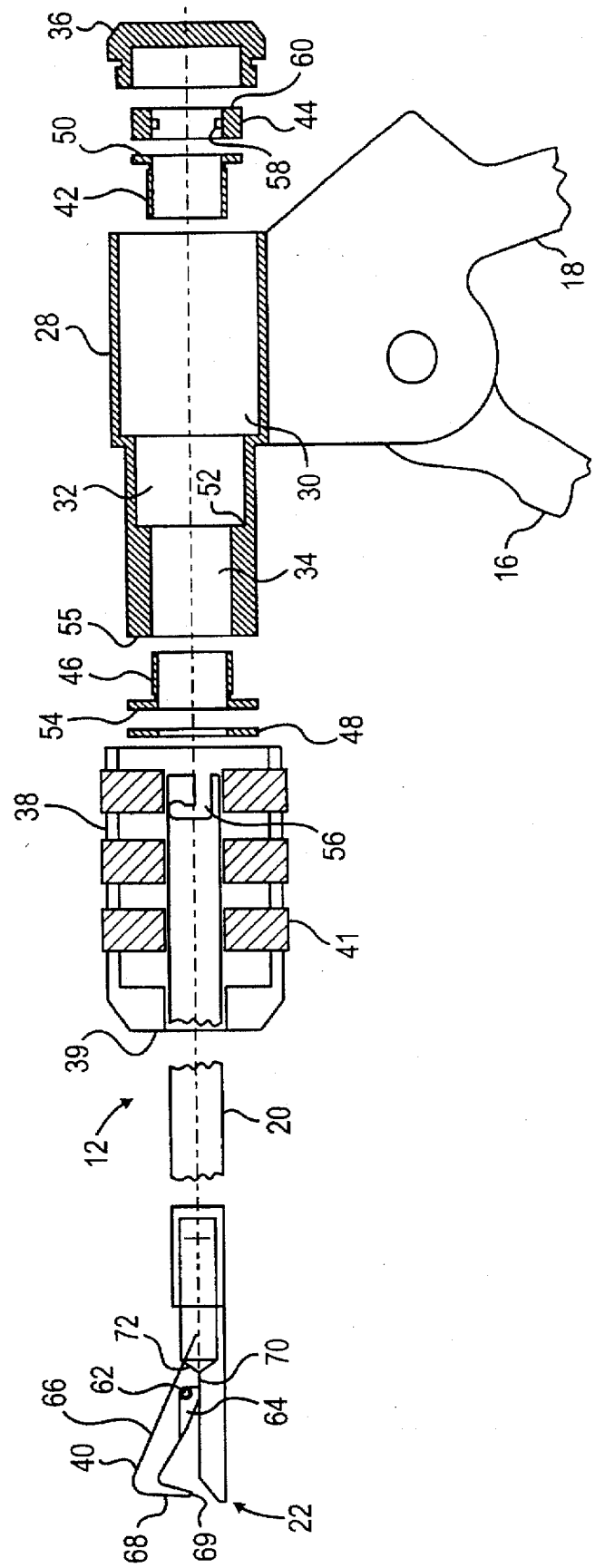
FIG. 4 is an exploded side elevational view of the barrel assembly and the handle assembly in accordance with the present invention.

As best seen in FIGS. 1 through 4, the handle assembly 14 is formed of trigger 16 and a handle body 24 with depending handle 18. The trigger is pivotally mounted to the handle body by a mounting pin 26. The handle body includes a housing barrel 28 for receiving the barrel assembly 12. Preferably, the housing barrel 28 is integrally formed with the handle body 24. As shown in FIG. 4, the housing barrel 28 has first, second and third chambers 30, 32 and 34 with consecutively decreasing internal diameters.

FIG. 3 is an isolated view of the trigger 16 showing its contour shape and an abutting end 25. The abutting end is positioned in the housing barrel 28 as shown in FIG. 1 and moves back and forth within the first chamber 30 as the trigger is actuated. As the trigger is squeezed, the abutting end rotates in a counterclockwise direction about pin 26 to force the shaft 23 in the forward direction.

Figure 2:
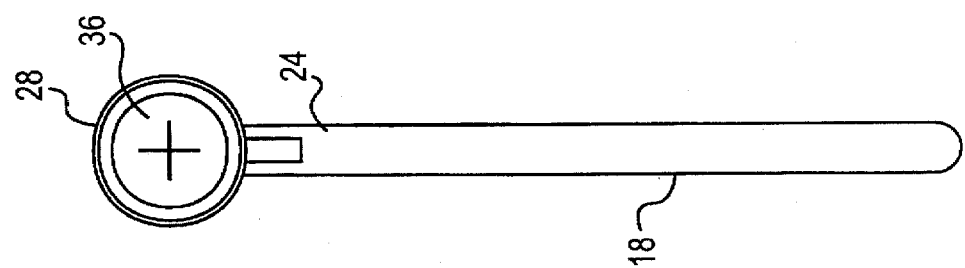
FIG. 2 is a rear elevational view of a proximal end of the ligation clip remover in accordance with the present invention.

An end cap 36 is screw-threaded onto a proximal end of the first chamber 30 to close the housing barrel 28. The end cap also serves as a stop for the abutting end 25 of the trigger, which is biased in a rearward direction, i.e., clockwise about pin 26, by the shaft 23 as discussed in detail below. FIG. 2 is a rear view of the ligation clip remover illustrating the slender design of the handle body 24 and the housing barrel 28.

Details of the barrel assembly 12 will be discussed primarily with reference to FIGS. 1 and 4. The barrel assembly includes an elongated, slender barrel 20 for housing the shaft 23, which is part of a shaft assembly, and a collar 38 rotatably secured to the housing barrel 28 of the handle assembly 14. The collar is welded or otherwise secured to the proximal end of the elongated barrel to move in unison therewith. The collar is also provided with knurled rings 41, or other comparable means, to assist the user in gripping and rotating the collar. The clip separating mechanism 22 is mounted at the distal end of the elongated barrel and will be discussed in detail below.

To secure the collar 38 to the handle assembly 14, a rear bushing 42 and a bayonet lock ring 44 are inserted through the proximal end of the housing barrel 28, i.e., through the first chamber 30, and a front bushing 46 is received in the distal end of the housing barrel, i.e., into the third chamber 34. When positioned in the housing barrel 28, a rim 50 on the rear bushing rests against a stepped portion 52 between the second chamber 32 and third chamber 34, and a rim 54 on the front bushing rests against a front face 55 of the third chamber 34. A curved washer, or flat spring, 48 is positioned against the rim 54 on the front bushing. The proximal end of the slender barrel 20 is provided with two oppositely disposed "J-shape", or bayonet-type, slots 56 for receiving internal pins 58 on the bayonet lock ring 44.

To assemble the barrel assembly on the handle assembly, the forward bushing 46 and flat spring 48 are inserted in an open end of the collar 38 and over the proximal end of the slender barrel 20. The collar 38 is then slipped over the distal end of the housing barrel 28 until the rim 54 on the front bushing 46 abuts the front face 55 of the third chamber. With the bayonet lock ring 44 and rear bushing 42 positioned in the housing barrel 28, the bayonet slots are aligned with the internal pins 58 and, with the help of a supplemental tool to stabilize the lock ring, an axial compressive force against the bias of flat spring 48 is applied to the collar to slide the bayonet slots relative to the internal pins. When the pins reach the end of a longitudinal portion of the bayonet slots, the lock ring is rotated relative to the collar to slide the pins along a lateral portion of the bayonet slots. When the pins reach the far end of the lateral portions, the compressive force is released and the flat spring 48 will force the lock ring and collar in opposite axial directions. The internal pins are thus secured in a terminal end of the bayonet slots, i.e., in the tip of the "J-shaped" slots, and the barrel assembly is rotatably secured to the handle assembly. The supplemental tool, which is used to assemble and disassemble the apparatus, has two pins for engaging holes 60 in the lock ring 44, and is used to prevent the lock ring from moving in the axial direction when the compressive force is applied and also to rotate the lock ring relative to the collar.

Figure 6:
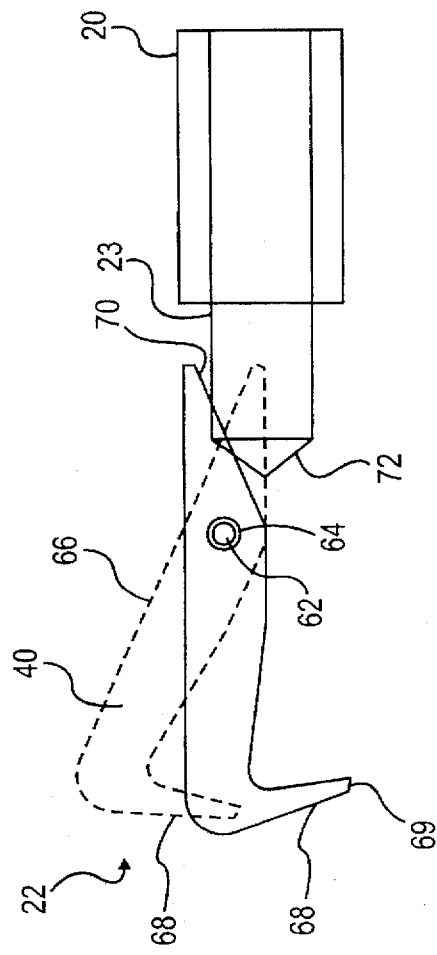
FIG. 6 is a side elevational view of a distal end of the barrel assembly in accordance with the present invention, showing a clip separator in both the open and closed positions.
Figure 7:
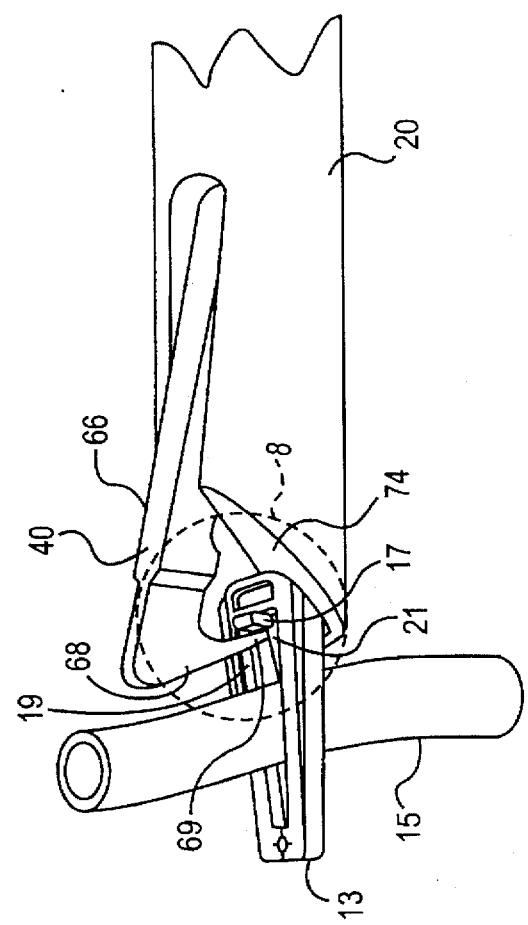
FIG. 7 is a perspective view of the clip separator in position with a closed ligation clip in accordance with the present invention.
Figure 9:
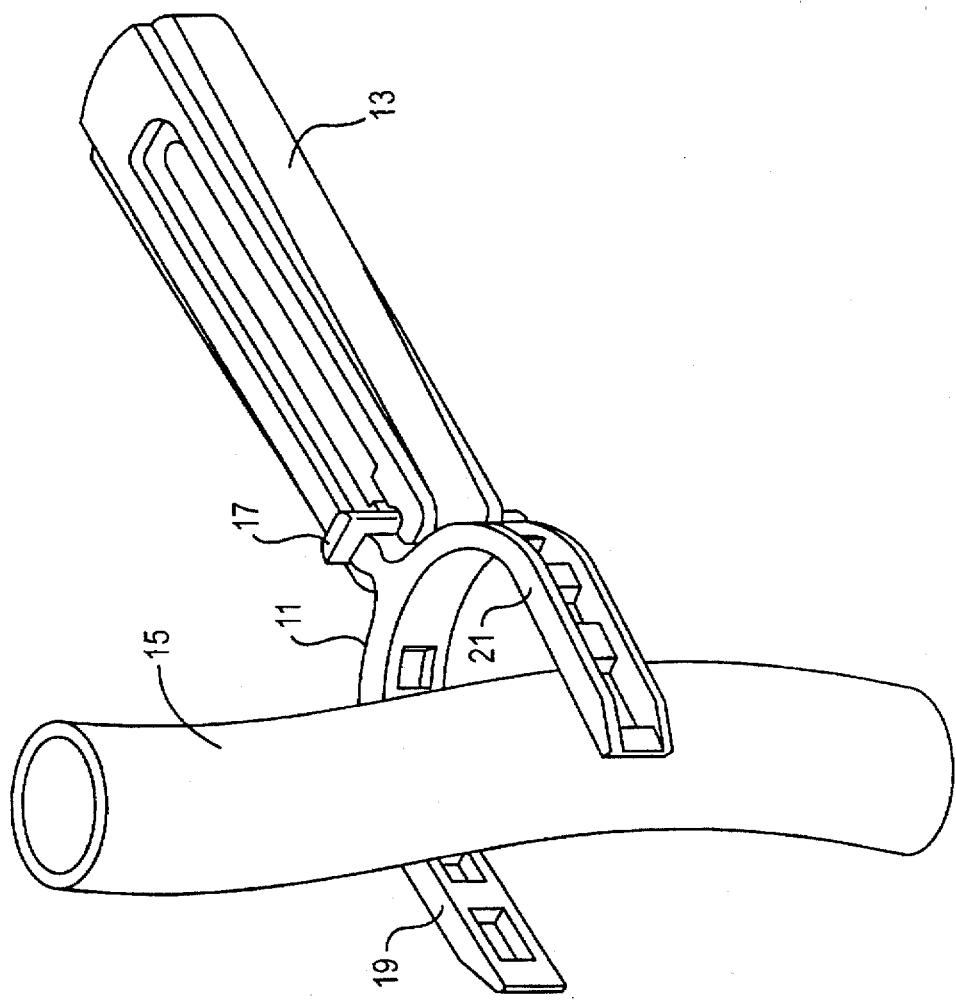
FIG. 9 is a perspective view of a two-piece ligation clip positioned around a vessel to be ligated.
Figure 10:
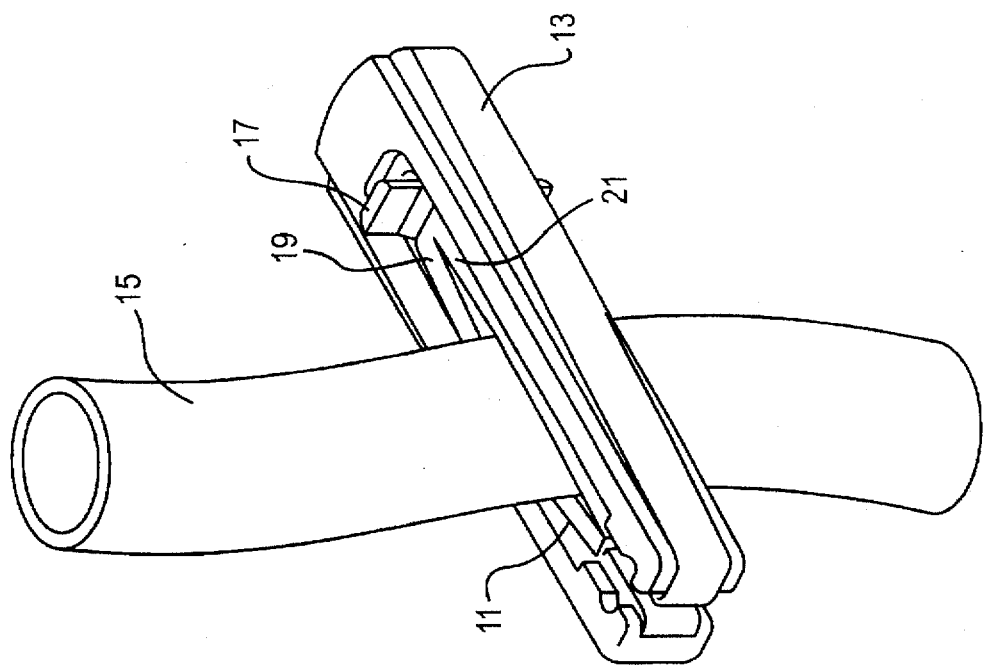
FIG. 10 is a perspective view of the two-piece ligation clip closed around the vessel.

The clip separating mechanism 22 is secured to the distal end of the slender barrel 20 as shown in FIGS. 1, 4 and 7. FIG. 4 is a schematic-type drawing of the clip separating mechanism, while FIGS. 1 and 7 are a top plan view and a perspective view, respectively, of the clip separating mechanism in accordance with the present invention. FIG. 6 is side elevational view of a distal end of the barrel assembly with a portion of the slender barrel 20 cut away to show the clip separating mechanism 22 in both the open and closed positions. As best seen in FIGS. 4 and 6, the clip separating mechanism is comprised of a spreader 40 pivotally mounted about a pin 62 secured in the barrel 20 and biased by spring 64 to rest in an open position. The one-piece spreader 40 is shaped to have a lever portion 66 and a hooked nose portion 68 narrowing to form a substantially pointed terminal end 69.

The proximal end of the lever 66 has an angled cam surface 70 for receiving a rounded end 72 of the sliding shaft 23. When the shaft slides in the forward direction, i.e., toward the distal end, the rounded end 72 abuts the cam surface 70 and pivots the lever about pin 62 to lower the nose portion 68.

The distal end of the elongated barrel 20 terminates in a slanted face 74, best seen in FIG. 7, and a flat, slotted area 76, best seen in FIG. 1, in which a closed ligation clip can rest. It is preferable to apply a non-reflective coating to the distal half or third of the barrel assembly 12 to reduce glare and reflection of light inside the patient's body during the surgical procedure. The spreader 40 itself is also preferably coated with a non-reflective substance for the same reason.

Figure 5:
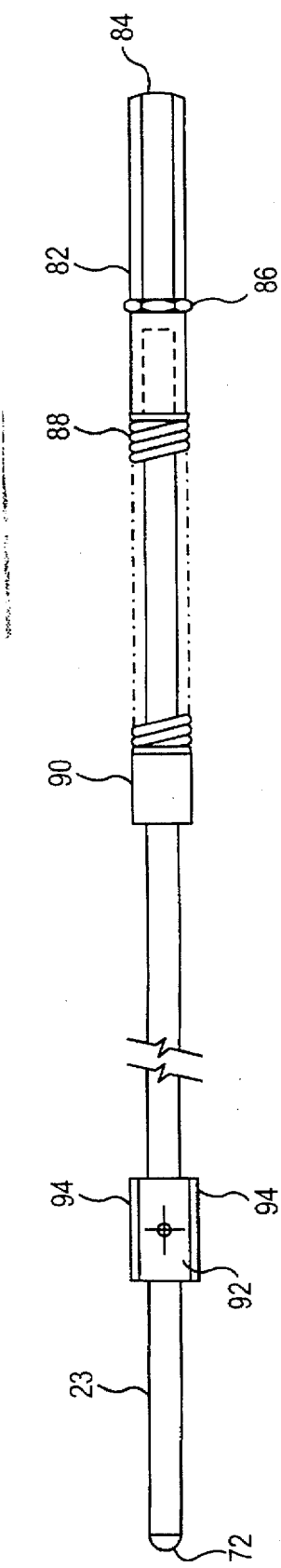
FIG. 5 is a side elevational view of a shaft assembly in accordance with the present invention.

A shaft assembly 78 is housed in the barrel assembly and will be described in detail with reference to FIG. 5. The shaft assembly is formed of the slender, elongated shaft 23, with the shaft having the rounded end 72 at its distal end and an enlarged diameter portion 82 at its proximal end. The enlarged diameter end also has a rounded end 84 that is engaged by the abutting end 25 of the trigger 16 as shown in FIG. 1. An elastic O-ring 86 is positioned in a groove in the enlarged diameter end and helps to prevent leakage from the pressurized internal body cavity. A compression spring 88 is mounted on the shaft 23 between a distal side of the enlarged diameter end 82 and a spring retainer 90. The spring retainer is tubular in shape and slides freely on the shaft 23.

An internal pin (unshown in the drawings) provided on the internal surface of the elongated barrel 20 abuts against a distal end of the spring retainer when the shaft assembly is mounted within the barrel assembly. In this manner, distal movement of the spring retainer is limited. When abutting against the internal pin, the spring retainer functions as a stop against which the spring 88 is compressed as the shaft 23 slides forwardly toward the distal end of the barrel assembly. At the distal portion of the shaft 23 is mounted a fixed bearing 92 for ensuring smooth, linear movement. The fixed bearing includes one or preferably two flat sides 94 for enabling it to slide past the internal pin when the shaft assembly is inserted in the barrel assembly through the open end of the housing barrel 28.

In one preferred embodiment, the shaft assembly measures a total length of approximately 12 inches, with the shaft 23 extending approximately 9.5 inches from the enlarged-diameter end 82 and having a round cross-sectional of approximately 0.22 inches. Of course, these dimensions are arbitrary and are determined by taking into consideration the dimensions of the barrel and handle assemblies.

Figure 8:
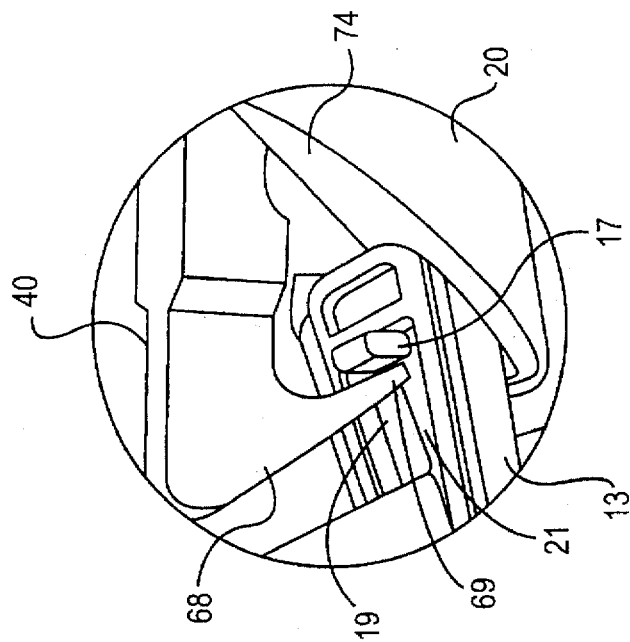
FIG. 8 is a detailed perspective view of an isolated portion of FIG. 7.

In use, the ligation clip remover is inserted into the patient's body through a cannula and positioned proximate to a closed ligation clip to be removed. The trigger 16 is squeezed while inserting the remover through the cannula to maintain the spreader 40 in the closed position. As best seen in FIGS. 7 and 8, the clip remover is maneuvered to position the nose portion 68 of the spreader 40 immediately in front of the trunnion 17 at the base of the closed arms 19 and 21. In this position, the end of the closed ligation clip is supported on the flat area 76 of the barrel assembly.

The clip remover is now ready to remove the closed ligation clip. To actuate the clip remover, the trigger is squeezed to rotate the abutting end 25 in the counterclockwise direction about pin 26 and force the shaft 23 in the forward direction. With this forward movement, the rounded end 72 of the shaft engages the cam surface 70 of the lever and rotates it counterclockwise about pin 62. This forces the pointed end 69 of the nose portion downwardly and between the closed arms 19 and 21. The closed arms are thus forced apart by the downward force of the nose portion, and the compressive force on the ligated vessel is released. The ligation clip can then be manipulated to slide off an open end of the vessel.

As the shaft assembly is actuated in the forward direction, the shaft 23 slides relative to the spring retainer 90 retained by the internal pin. Therefore, spring 88 becomes compressed and provides a biasing force against the forward movement of the shaft assembly. When the trigger is released the charged spring forces the shaft assembly in the rearward direction to retract the shaft and force the trigger to its unbiased, at rest, position. As the shaft moves rearwardly the spreader 40 is biased back to its open position by spring 64.

Although a specific embodiment of the present invention has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A ligation clip remover, comprising:
   a handle assembly with a squeezable trigger;
   a barrel assembly rotatably connected to said handle assembly, with said barrel assembly including a stationary portion at its distal end for receiving a ligation clip;
   a shaft slidably housed in said barrel assembly and slidable by actuation of said trigger; and
   a clip separator engaged to a distal portion of said barrel assembly, said separator having a lever pivotably mounted in said barrel assembly, wherein said separator is actuated by said sliding shaft to move a distal end of said lever toward said stationary portion of said barrel assembly.

2. A ligation clip remover according to claim 1, wherein said barrel assembly includes bayonet-type slot engaging means for rotatably engaging said barrel assembly to said handle assembly and permitting it to rotate freely about its longitudinal axis.

3. A ligation clip remover according to claim 1, further comprising a shaft assembly, with said shaft being part of said shaft assembly and said shaft having an enlarged-diameter proximal end operably engaged with said trigger, wherein actuation of said trigger slides said shaft assembly in a forward direction to close said clip separator.

4. A ligation clip remover according to claim 3, wherein said shaft assembly further includes a biasing spring mounted on said shaft for biasing said shaft assembly in a rearward direction.

5. A ligation clip remover according to claim 1, wherein said lever has a proximal cam surface for engagement by said sliding shaft and a downwardly-extending nose at its distal end.

6. A ligation clip remover according to claim 5, wherein said clip separator includes a spring mounted in said barrel assembly for biasing said lever in an open position.

7. A ligation clip remover according to claim 5, wherein said downwardly-extending nose is positioned opposite to said distal end of said barrel assembly, and said separator is actuated to move said nose to approach said barrel assembly.

8. A ligation clip remover according to claim 1, wherein said stationary portion includes a slanted face and a flat slotted portion for receiving the ligation clip.

9. A ligation clip remover according to claim 8, wherein said lever has a downwardly-extending nose at its distal end, and said separator is actuated to move said nose toward said flat slotted portion.

10. A ligation clip remover for removing a closed two-piece ligation clip having first and second arms, comprising:

a handle assembly having a squeezable trigger;

a barrel assembly rotatably connected at its proximal end to said handle assembly with said barrel assembly including a stationary portion at its distal end for receiving a ligation clip;

clip separating means, secured in a distal portion of said barrel, for separating the closed ligation clip, said clip separating means including a lever pivotably mounted in said barrel assembly; and actuating means, disposed within said barrel assembly, for actuating said clip separating means when said trigger is squeezed to move a distal end of said lever toward said stationary portion of said barrel assembly.

11. A ligation clip remover according to claim 10, wherein said barrel assembly includes bayonet-type slot engaging means for rotatably engaging said barrel assembly to said handle assembly and permitting said barrel assembly to rotate freely about its longitudinal axis.

12. A ligation clip remover according to claim 10, wherein said actuating means includes an extended shaft with an enlarged-diameter section at its proximal end, said enlarged diameter section operably engaged with said trigger such that said shaft slides in a forward direction in said barrel assembly when said trigger is squeezed.

13. A ligation clip remover according to claim 12, wherein said actuation means further includes a biasing spring mounted on said shaft for biasing said actuating means in a rearward direction.

14. A ligation clip remover according to claim 10, wherein said lever has a proximal cam surface for engagement by said actuating means and a hooked nose for separating the first and second arms of the closed ligation clip.

15. A ligation clip remover according to claim 14, wherein said hooked nose terminates in a pointed end, and said actuating means slides forward in said barrel assembly to pivot said lever and force said pointed end between the first and second arms of the closed ligation clip.

16. A ligation clip remover according to claim 15, wherein said clip separating means further includes a spring mounted in said barrel assembly for biasing said lever in an open position.

17. A ligation clip remover according to claim 14, wherein said downwardly-extending nose is positioned opposite to said distal end of said barrel assembly, and said separator is actuated to move said nose to approach said barrel assembly.

18. A ligation clip remover according to claim 10, wherein said stationary portion includes a slanted face and a flat slotted portion for receiving the ligation clip.

19. A ligation clip remover according to claim 18, wherein said lever has a downwardly-extending nose at its distal end and said separator is actuated to move said nose toward said flat slotted portion.

20. A ligation clip remover, comprising:

a handle having an actuator;

extended barrel means connected to said handle, with said barrel means including a stationary portion at its distal end for receiving a ligation clip;

clip separating means, secured in a distal portion of said barrel means, for separating a closed ligation clip, said clip separating means including a lever pivotably mounted in said barrel means; and actuating means slidably housed in said barrel means and operable by said actuator to actuate said clip separating means to move a distal end of said lever toward said stationary portion of said barrel means.

21. A ligation clip remover according to claim 20, further comprising rotatable connecting means for rotatably connecting said barrel means to said handle and permitting said barrel means to rotate freely about its longitudinal axis with respect to said handle.

22. A ligation clip remover according to claim 21, wherein said rotatable connecting means includes bayonet-type slots in a proximal end of said barrel means and a lock ring with internal pins for engaging said slots.

23. A ligation clip remover according to claim 20, wherein said actuating means includes a slender shaft with an enlarged-diameter section at its proximal end, with said enlarged diameter section operably engaged with said actuator such that said shaft slides in a forward direction in said barrel assembly when said actuator is actuated.

24. A ligation clip remover according to claim 23, wherein said actuation means further includes a biasing spring mounted on said shaft for biasing said actuating means in a rearward direction.

25. A ligation clip remover according to claim 20, wherein said lever has a proximal cam surface for engagement by said actuating means and a hooked nose for separating two close members of a ligation clip.

26. A ligation clip remover according to claim 25, wherein said hooked nose terminates in a pointed end, and said actuating means slides forward in said barrel means to pivot said lever and force said pointed end between the two closed members.

27. A ligation clip remover according to claim 26, wherein said clip separating means further includes biasing means mounted on said barrel means for biasing said lever in an open position.

28. A ligation clip remover according to claim 25, wherein said downwardly-extending nose is positioned opposite to said distal end of said barrel means, and said separator is actuated to move said nose to approach said barrel means.

29. A ligation clip remover according to claim 20, wherein said stationary portion includes a slanted face and a flat slotted portion for receiving the ligation clip.

30. A ligation clip remover according to claim 29, wherein said lever has a downwardly-extending nose at its distal end and said separator is actuated to move said nose toward said flat slotted portion.

* * * * *

UNITED STATES PATENT AND TRADEMARK OFFICE
CERTIFICATE OF CORRECTION

PATENT NO. : 5,707,377

DATED : January 13, 1998

INVENTOR(S): JOHN W. KELLER ET AL.

It is certified that error appears in the above-identified patent and that said Letters Patent is hereby corrected as shown below:

Title page
[56] REFERENCES CITED

U.S. Patent Documents
"4,602,631  7/1986 Kunatsu" should read
--4,602,631  7/1986 Funatsu--.

COLUMN 4

Line 51, "is" should read --is a--.

COLUMN 7

Line 7, "assembly with" should read --assembly, with--.

COLUMN 8

Line 36, "close" should read --closed--.

Signed and Sealed this

Twenty-fifth Day of August, 1998

Attest:

BRUCE LEHMAN

Attesting Officer

Commissioner of Patents and Trademarks